(12) United States Patent
McCallum

(10) Patent No.: US 12,318,213 B2
(45) Date of Patent: Jun. 3, 2025

(54) APPARATUS AND METHODS FOR DETECTING INCORRECT MUSCLE USE AND/OR POSTURE

(71) Applicant: Sadie McCallum, Weare, NH (US)

(72) Inventor: Sadie McCallum, Weare, NH (US)

( * ) Notice: Subject to any disclaimer, the term of this patent is extended or adjusted under 35 U.S.C. 154(b) by 673 days.

(21) Appl. No.: 17/683,492

(22) Filed: Mar. 1, 2022

(65) Prior Publication Data

US 2022/0273231 A1 Sep. 1, 2022

Related U.S. Application Data

(60) Provisional application No. 63/155,031, filed on Mar. 1, 2021.

(51) Int. Cl.
*A61B 5/00* (2006.01)

(52) U.S. Cl.
CPC .......... *A61B 5/4561* (2013.01); *A61B 5/6804* (2013.01); *A61B 5/746* (2013.01); *A61B 2560/0223* (2013.01)

(58) Field of Classification Search
CPC ..... A61B 5/4561; A61B 5/6804; A61B 5/746; A61B 2560/0223; A61B 5/4082; A61B 5/4519; A61B 5/6823; A61B 5/742; A61B 5/7455; A61B 5/1116; A61B 5/103; A61B 5/11; A61B 5/1126; A61B 2562/0219
See application file for complete search history.

(56) References Cited

U.S. PATENT DOCUMENTS

| | | | |
|---|---|---|---|
| 5,402,107 A * | 3/1995 | Rencavage | A61B 5/1116 600/595 |
| 8,928,484 B2 | 1/2015 | Chang et al. | |
| 9,439,599 B2 | 9/2016 | Thompson et al. | |
| D852,656 S | 7/2019 | Kazes et al. | |
| 2001/0007923 A1* | 7/2001 | Yamamoto | A61B 5/103 600/587 |
| 2002/0032386 A1* | 3/2002 | Sackner | A61B 5/1135 600/509 |
| 2006/0161363 A1* | 7/2006 | Shibasaki | G01C 19/5607 702/94 |
| 2006/0195051 A1* | 8/2006 | Schnapp | A61B 5/6822 600/595 |
| 2008/0100459 A1* | 5/2008 | Hoffman | A61B 5/1116 340/573.7 |
| 2008/0228432 A1* | 9/2008 | Ha | G06F 1/1626 702/150 |
| 2009/0054814 A1* | 2/2009 | Schnapp | A61B 5/1116 600/595 |

(Continued)

FOREIGN PATENT DOCUMENTS

GB 2492754 A1 1/2013

*Primary Examiner* — Ryan W Sherwin
(74) *Attorney, Agent, or Firm* — COOLEY LLP

(57) ABSTRACT

Provided is a device comprising a sensor to detect deviation of muscle position in a user. The device includes a first housing portion having at least one sensor and at least one signaling mechanism to alert a user and a second housing portion rotatably coupled to the first housing portion. The second housing portion has an attachment element to maintain the device on the user. The sensitivity of the device can be configured to respond to incorrect muscle position and the sensitivity of the device can be calibrated through rotating the first housing portion with respect to the second housing portion.

20 Claims, 9 Drawing Sheets

(56) References Cited

U.S. PATENT DOCUMENTS

| | | | |
|---|---|---|---|
| 2010/0117837 A1* | 5/2010 | Stirling | A61B 5/11 382/107 |
| 2013/0274587 A1* | 10/2013 | Coza | G16H 40/67 600/595 |
| 2015/0057971 A1* | 2/2015 | Grenet | G06F 3/011 702/152 |
| 2015/0276793 A1* | 10/2015 | Takenaka | A61B 5/1121 73/504.03 |
| 2015/0374266 A1 | 12/2015 | Cohen et al. | |
| 2018/0220966 A1 | 8/2018 | Cohen et al. | |
| 2019/0183388 A1 | 6/2019 | Cohen et al. | |

\* cited by examiner

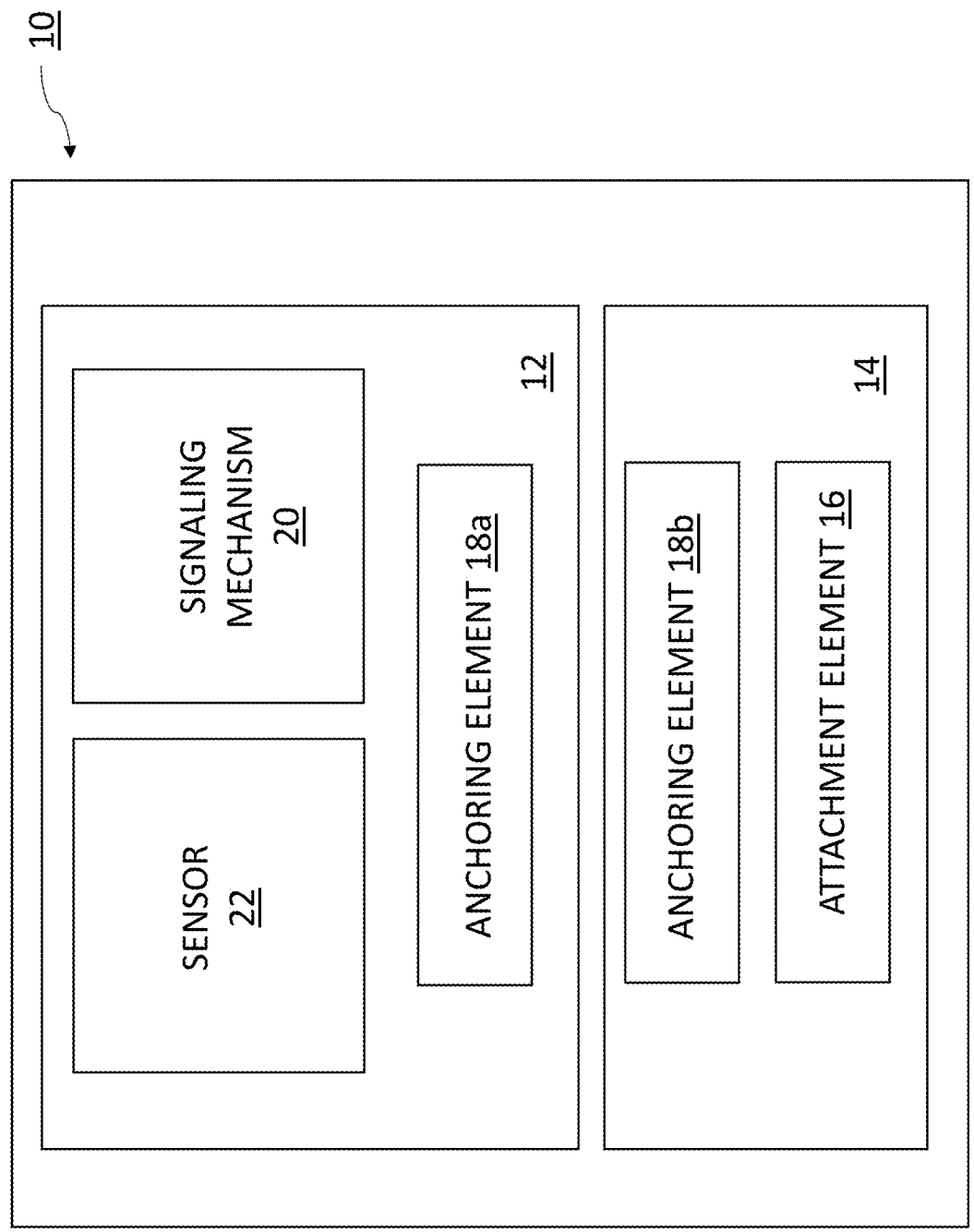

APPARATUS AND METHODS FOR DETECTING INCORRECT MUSCLE USE AND/OR POSTURE

CROSS-REFERENCE TO RELATED APPLICATION

This application claims priority to and the benefit of U.S. Provisional Patent Application No. 63/155,031, filed Mar. 1, 2021 and titled "Apparatus and Methods for Detecting Incorrect Muscle Use and/or Posture", which is incorporated herein by reference in its entirety.

BACKGROUND

Movement impairment syndromes are characterized by sustained alignment in a non-ideal position and impairment of muscle tone, gross and fine motor functions, balance, control, coordination, reflexes, and posture. Treatment is based on correcting the impaired alignment and movement patterns. For patients with cerebral palsy, surgery can improve movement and alignment in the legs, ankles, feet, hips, wrists and arms, and some doctors recommend physical therapy before and after the surgery. However, slouching, crouching, wrong muscle use, and overcompensating with the wrong muscle complicate therapeutic timelines and may render the effectiveness of physical therapy inconsistent. There is hence a need for an alignment correcting and symmetrical muscle building device that alerts a user of deviation from desired muscle position.

SUMMARY

In one aspect, the present disclosure relates to a device including a first housing portion having a tilt switch, a vibrating element, and a visual indication device, and a second housing portion rotatably coupled to the first housing portion. In some aspects, the first housing portion is spherical and/or the second housing portion has an attachment element configured to couple the second housing portion to the user. In some aspects, the tilt switch is configured to detect deviation of a muscle position of a user when the attachment element couples the second housing portion to the user, and the vibrating element is configured to provide a haptic indication and the visual indication device is configured to provide a visual indication in response to the tilt switch detecting deviation of the muscle position of the user by a predetermined amount. In some aspects, the predetermined amount is configured to be calibrated through rotating the first housing portion with respect to the second housing portion.

BRIEF DESCRIPTION OF FIGURES

FIG. 1 is a schematic illustration of a device having a housing with two separate portions, according to an embodiment;

DETAILED DESCRIPTION

Figure 2A:
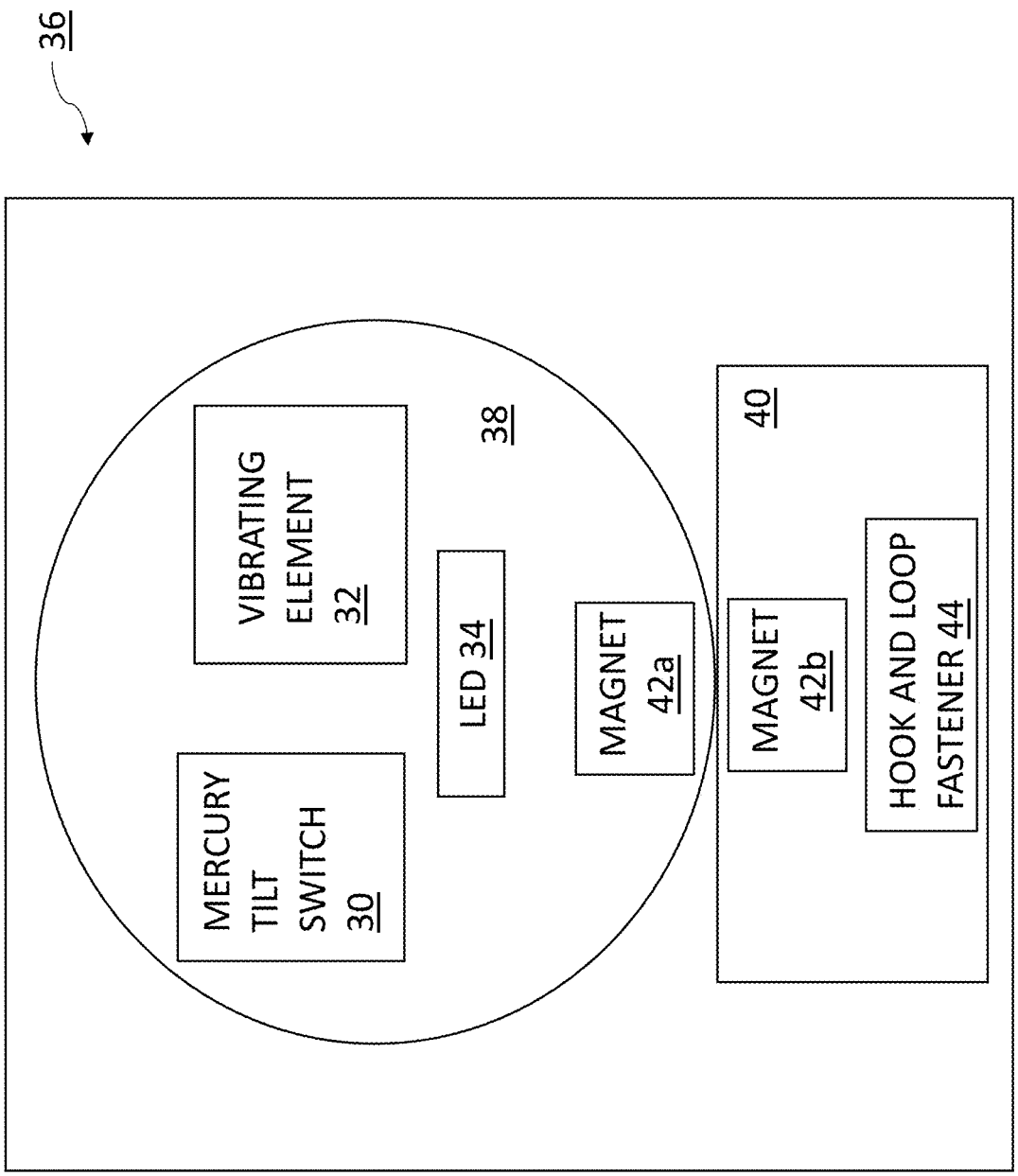
FIGS. 2A and 2B are schematic illustrations of a device having a first housing portion rotatably coupled to a second housing portion, according to an embodiment.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description is for the purpose of describing particular embodiments only and is not intended The present disclosure provides a device comprising a first housing portion having a tilt switch, a vibrating element, and a visual indication device. In some aspects, the first housing portion is spherical. In some aspects, the second housing portion is rotatably coupled to the first housing portion. In some aspects, the second housing portion has an attachment element which is configured to couple the second housing portion to a user. In some aspects, the tilt switch is fixedly mounted in the first housing portion and senses a change in position of the first housing portion, wherein the tilt switch configured to detect deviation of a muscle position of the user relative to a desired muscle position of the user. In some aspects, the tilt switch configured to detect deviation of a muscle position of the user when the attachment element couples the second housing portion to the user. In some aspects, the vibrating element is configured to provide a haptic indication and the visual indication device is configured to provide a visual indication in response to the tilt switch detecting deviation from the desired muscle position of the user by a predetermined amount. In some aspects, the predetermined amount is configured to be adjusted through rotating the first housing portion with respect to the second housing portion.

In some aspects, the second housing portion of the device is coin shaped.

In some aspects, the attachment element includes a portion of a hook and loop fastener.

In some aspects, the first housing portion includes a first magnet, and the second housing portion includes a second magnet, wherein the second housing portion is rotatably coupled to the first housing portion using the first magnet and the second magnet.

In some aspects, the first housing portion is rotatably coupled to the second housing portion using at least one magnet.

In some aspects, the first housing portion includes a first magnet, and the second housing portion includes a second magnet, wherein the first magnet is configured to freely reposition within the first housing portion.

In some aspects, deviation from a desired muscle position moves the tilt switch with respect to a predetermined axis associated with the neutral position.

In some aspects, the rotation of the first housing portion with respect to the second housing portion alters a rotational distance between the neutral tilt switch position and a triggered tilt switch position, wherein the triggered tilt switch position is associated with a predetermined amount of deviation from the desired muscle position.

In some aspects, the position of the tilt switch may deviate with respect to a neutral tilt switch position as the first housing portion rotates with respect to the second housing portion.

In some aspects, the rotation of the first housing portion with respect to the second housing portion alters a rotational distance between the neutral tilt switch position and a triggered tilt switch position, wherein the triggered tilt switch position is associated with a predetermined amount of deviation from the desired muscle position.

In some aspects, the attachment element includes a portion of a fastener that is configured to removably couple, in a user-selected orientation, the second housing portion to a garment, wherein the garment wearable by the user.

In some aspects, the garment includes a portion of the fastener to removably couple the device to the user in a user-selected orientation when the user wears the garment.

In some aspects, the fastener is at least one of a hook and loop fastener, a clip, a pocket, a pin, a buckle, snaps, grommets, or snap hooks.

The present disclosure provides a method comprising positioning a device on a user, the device having a sensor including a tilt switch for detecting deviation from a desired muscle position in the user. The method comprises calibrating the sensitivity of the device through rotating a first housing portion with respect to a second housing portion. In some aspects, the second housing portion has an attachment element configured to attach the second housing portion to the user. In some aspects, the first housing portion has a sensor, a vibrating element, and a visual indication device. In some aspects, the first housing portion is spherical. In some aspects, the device generates predetermined feedback to the user through the vibrating element and the visual indication device in response to deviation from the desired muscle position by a predetermined amount.

In some aspects, positioning of the attachment element may be adjusted by removably coupling the second housing portion to a garment wearable by the user. In some aspects, the attachment element is removably coupled using a fastener and in a user-selected orientation.

In some aspects, the fastener is at least one of a hook and loop fastener, a clip, a pocket, a pin, a buckle, snaps, grommets, or snap hooks.

The present disclosure provides a system, comprising a plurality of devices, each device from the plurality of devices being coupled to a user at a different body portion than the remaining devices from the plurality of devices.

In some aspects, each device from the plurality of devices includes a spherical first housing portion having a tilt switch, a vibrating element, and a visual indication device. In some aspects, each device from the plurality of devices includes a second housing portion rotatably coupled to the first housing portion, wherein the second housing portion has an attachment element configured to couple the second housing portion to a body portion of the user.

In some aspects, each device from the plurality of devices includes a tilt switch which is configured to detect deviation of a muscle position of the user when the attachment element couples the second housing portion to the user.

In some aspects, each device from the plurality of devices includes a vibrating element which is configured to provide a haptic indication and the visual indication device is configured to provide a visual indication in response to the tilt switch detecting deviation of the muscle position of the user by a predetermined amount, and wherein the predetermined amount is configured to be adjusted through rotating the first housing portion with respect to the second housing portion.

In some aspects, the position of the tilt switch of each device from the plurality of devices changes with respect to a neutral tilt switch position as the user moves.

In some aspects, the rotation of the first housing portion with respect to the second housing portion alters a rotational distance between a neutral tilt switch position and a triggered tilt switch position, wherein the triggered tilt switch position is associated with deviation of the muscle position by the predetermined amount.

In some aspects, the attachment element of each device includes a portion of a fastener that is configured to removably couple, in a user-selected orientation, the second housing portion to a garment wearable by the user.

In some embodiments, the present disclosure relates to a device having a sensor to detect deviation of muscle position in a user. A first housing portion of the device has at least one sensor and at least one signaling mechanism to alert a user. A second housing portion is rotatably coupled to the first housing portion and has an attachment element to maintain the device on the user. A sensitivity of the device is configured to respond to incorrect muscle position. The sensitivity of the device is calibrated through rotating the first housing portion with respect to the second housing portion.

In some embodiments, the device further includes a power source. In some embodiments, the power source is a battery, capacitor, an electrical outlet, a solar power converter, and/or the like.

In some embodiments, the attachment element includes a portion of a fastener that is configured to removably couple, in a user-selected orientation, the second portion of the housing to a garment. In some embodiments, the garment includes a portion of a fastener to removably couple the device to the user in a user-selected orientation. In some embodiments, the fastener is a hook and loop fastener, a clip, a pocket, a pin, a buckle, snaps, grommets, snap hooks, and/or the like.

In some embodiments, the sensitivity of the device may be reconfigured through rotating the first housing portion with respect to the second housing portion.

In some embodiments, a method includes positioning a device having a sensor for detecting deviation from a neutral muscle position in a user, calibrating sensitivity of the device through rotating a first housing portion having the sensor and at least one signaling mechanism with respect to a second housing portion having an attachment element, sensing an orientation of at least one body portion of the user, generating predetermined feedback to the user in response to deviation from the neutral muscle position, and adjusting sensitivity of the device by rotating the first housing portion with respect to the second housing portion. In some embodiments, the method further includes adjusting the positioning of the attachment element on a garment, in a user-selected orientation.

In some embodiments, a system includes a first device and a second device, wherein the first device detects deviation of muscle position in a first body portion and the second device detects deviation of muscle position in a second body portion.

A device 10 according to an embodiment is schematically illustrated in FIG. 1. The device 10 includes a housing with two separate portions. A first housing portion 12 includes a sensor 22, a signaling mechanism 20, and an anchoring element 18a. A second housing portion 14 includes an anchoring element 18b and an attachment element 16.

In some embodiments, any combination of device components described herein (e.g., sensor 22, signaling mechanism 20, anchoring elements 18a and 18b, and attachment element 16) may be arranged in either or both housing portions. For example, while the sensor 22 and signaling mechanism 20 are both shown in FIG. 1 as being in first housing portion 12, in some embodiments the sensor 22 and/or the signaling mechanism 20 can be in second housing portion 14.

In some embodiments, the first housing portion 12 can be provided in various shapes and configurations, including, but not limited to, cylindrical, flat, cube, sphere, prism, round, rectangular, square, oval, and/or the like. In some embodiments, the shape of the first housing portion 12 can be selected based on the desired movement of the device. For example, as described in further detail herein, if first housing portion 12 is a sphere, the first housing portion 12 can be configured to be rotated with respect to the second housing portion 14 in multiple different directions and/or at multiple different angles.

In some embodiments, the sensor 22 is configured to detect an orientation of at least one body portion of a user. In some embodiments, the sensor 22 detects deviation of muscle position in a user. For example, in some implementations, the sensor 22 can detect a deviation and/or change of an angle and/or position of the sensor. In some implementations, the sensor 22 is a switch which provides electricity to the signaling mechanism 20 upon detection of muscle deviation. In some implementations, the sensor 22 and signaling mechanism 20 can be in a first (neutral position) configuration positioned by the user such that the sensor 22 does not provide electricity to the signaling mechanism 20. This configuration by the user establishes a range of muscle deviations which do not activate the sensor 22. Upon deviation of muscle position outside of the range of the first configuration (e.g., more than a predetermined and/or user selected threshold), the sensor 22 and signaling mechanism 20 are activated and are in a second (deviated) configuration. More specifically, when the sensor 22 is activated and in the second configuration, the sensor 22 provides electricity to the signaling mechanism 20, which provides feedback to the user of the detected muscle deviation. Accordingly, the user can calibrate the device 10 such that the sensor 22 is in the first configuration when the user's body portion is in a desired and/or correct position and/or orientation and in the second configuration when the user's body portion had deviated from the desired and/or correct position and/or orientation by a predetermined and/or user-selected amount (e.g., more than a predetermined and/or user-selected threshold). In an embodiment, the user may adjust the device 10 such that the first configuration of the sensor 22 is closer to the deviated position, thereby decreasing the amount of user deviation required to reach the second configuration of the device and activate the sensor 22 and signaling mechanism 20.

In some embodiments, the sensor 22 can be a tilt switch (e.g., a mercury tilt switch), an accelerometer, a gyroscope, a tilt sensor and/or any other suitable sensor or combination of sensors. In some embodiments, the sensor 22 is configured for determining the orientation of the device 10 and whether that orientation has deviated more than a predetermined and/or user-selected amount.

In some embodiments, the signaling mechanism 20 is configured to generate predetermined feedback to the user in response to the sensor detecting a change in the orientation, angle and/or position of at least one body portion to which the device 10 is coupled. In some embodiments, the change in orientation is a deviation from a desired muscle position. In some embodiments, the feedback may include an alert, a vibration, an audible sound, a communication with a remote computing device (e.g., sending a signal to a smart phone, tablet, wearable, or other compute device), or any combination thereof. In some embodiments, the signaling mechanism 20 can be a vibrating element, a visual indication device (e.g., a light-emitting diode (LED) light bulb), a sound emitting device (e.g., speaker), or any combination thereof.

In some embodiments, the anchoring elements 18a and 18b can be magnets, clips, buckles, or adhesives suitable for removably securing the first housing portion 12 to the second housing portion 14. In some embodiments, the anchoring elements 18a and 18b are of a same type.

In some embodiments, the connection (e.g., magnetic, clip, adhesive, etc.) between the anchoring elements 18a and 18b allow the first and second housing portions to remain secured independent of the rotational positioning of the first housing portion with respect to the user and while the device is secured to the user via an attachment element 16. In some implementations, the rotational positioning is configured by the user to establish a first configuration for the sensor 22 and signaling mechanism 20. For example, in some implementations the anchoring element 18a and the anchoring element 18b can be magnets that allow the first housing portion 12 to rotate in multiple directions and/or degrees with respect to the second housing portion 14, as described in further detail herein.

Figure 5:
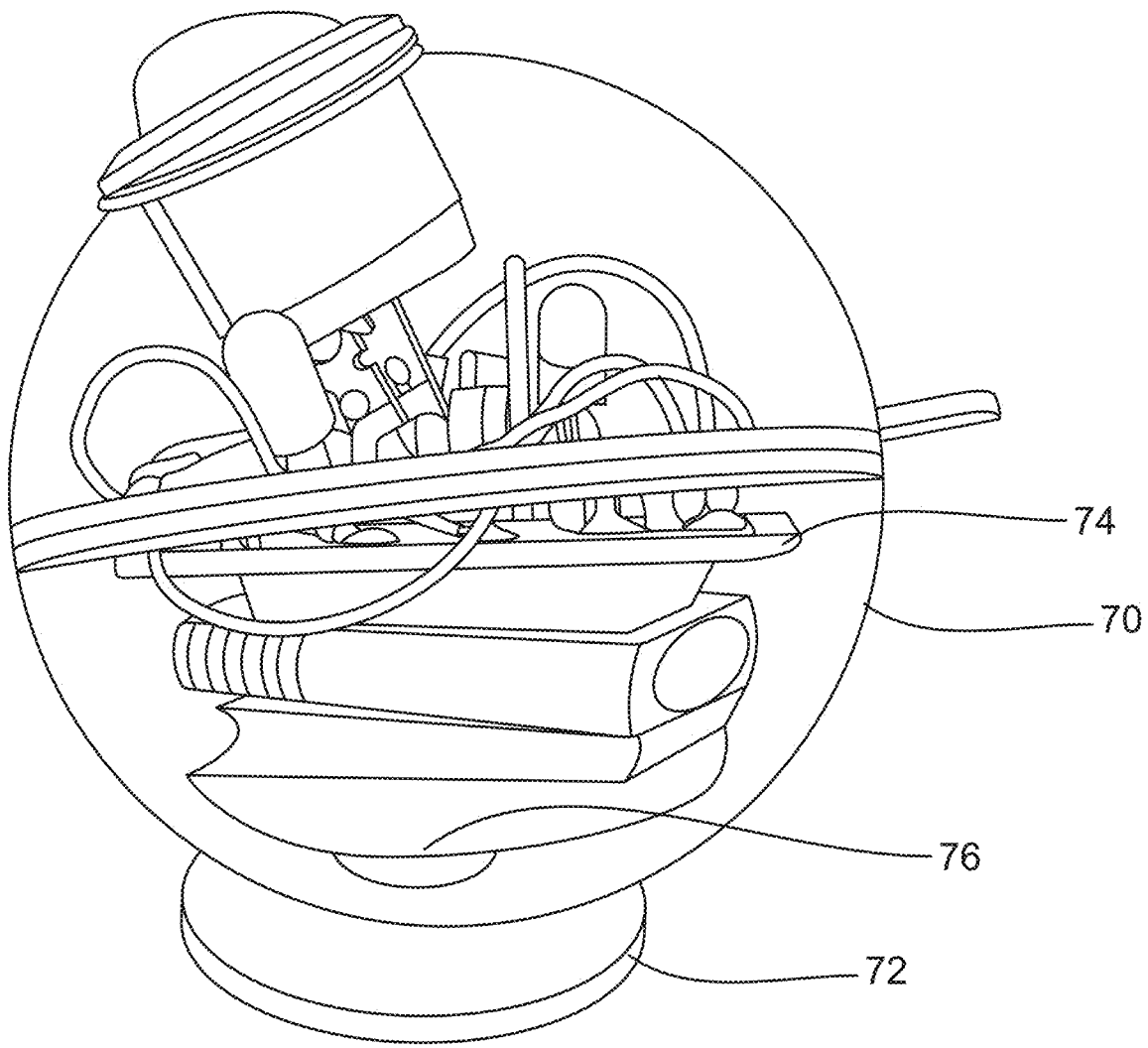
FIG. 5 illustrates a muscle position detection device, according to an embodiment.

In some embodiments, the second housing portion 14 can be provided in various shapes and configurations, including, but not limited to, cylindrical, flat, cube, sphere, prism, round, rectangular, square, oval, and/or the like. In some embodiments, the second housing portion 14 is of a shorter length compared to its width and is hence relatively flat (e.g., coin shaped), as shown in FIG. 5 (reference number 72).

In some embodiments, the attachment element 16 is used to maintain the device 10 on the user. In some embodiments, the attachment element 16 includes a portion of a fastener that is configured to removably couple, in a user-selected orientation, the second housing portion 14 to a garment. In some embodiments, the garment includes a portion of a fastener to removably couple the device to the user in a user-selected orientation. The positioning of the attachment element may be adjusted on a garment, in a user-selected orientation.

In some embodiments, the attachment element 16 can be a hook and loop fastener, for example as sold under the trade name VELCRO™. In some embodiments, the attachment element 16 can be a clip thereby facilitating the device to be attached to the garment, or one or more straps, enabling the user to wear the device 10 strapped around their body. In some embodiments, the attachment element 16 can be an adhesive suitable for removably securing the device to a garment on the user.

In some embodiments, calibration of the device 10 configures the sensitivity of the sensor 22, which in turn configures the signaling mechanism 20 alerting the user of their orientation (or deviation from their desired orientation). In some embodiments, calibration of the sensitivity of the device 10 alters when the device detects deviation of muscle position in a body portion. Similarly stated, calibration of the sensitivity of the device 10 determines at what position the sensor 22 moves from the first configuration to the second configuration. In response to the signaling mechanism 20 alerting the user, the user may adjust their orientation and muscle position to a desired position such that the sensor 22 moves from the second configuration to the first configuration, turning off the signaling mechanism 20. In some embodiments, the sensor 22 and signaling mechanism 20 are in a first configuration positioned by the user such that the sensor 22 does not provide electricity to the signaling mechanism 20. This configuration by the user establishes a range of muscle deviations that do not activate the sensor 22. In some implementations, the user may position the sensor 22 such that a wide range of muscle deviations do not activate the sensor 22 and in some implementations, the user may position the sensor 22 such that a narrow range of muscle deviations do not activate the sensor 22. Through adjusting the range of muscle deviations that do not activate the sensor 22, the user may calibrate the sensitivity of the device's detection and subsequent feedback.

In some embodiments, the second housing portion 14 is rotatably coupled to the first housing portion 14. In some embodiments, the sensitivity of the device is calibrated through rotating the first housing portion 12 with respect to the second housing portion 14. In some embodiments, sensitivity of the device is configured to respond to incorrect muscle position. In some embodiments, the position of the sensor 22 in the first housing portion 12 can be adjusted to multiple different angles or degrees relative to a body portion by rotating the first housing portion 12 with respect to the second housing portion 14. In some embodiments, the second housing portion 14 remains affixed while the first housing portion 12 is angularly displaced. In some implementations, for example, the user can twist the first housing portion with respect to the second housing portion 14 to an angle suitable for a first configuration of a particular body portion and subsequently twist the first housing portion 12 to a different angle suitable for a first configuration of a different body portion. In some embodiments, rotation of the first housing portion 12 displaces the sensor 22 such that a different muscle deviation and/or movement will activate the sensor 22 to switch from the first configuration to the second configuration. In some implementations, for example, the device may be configured to a first configuration defining a neutral position of a particular body portion and may subsequently be configured to a neutral position for a different body portion. In some implementations, for example, through rotation of the first housing portion with respect to the second housing portion, the device may be configured to varying neutral positions to increase or decrease the range of motion necessary to achieve positional deviation (e.g., deviation in rotational position) that will activate the sensor 22. In some embodiments, the sensitivity of the device 10 may be reconfigured through rotating the first housing portion 12 with respect to the second housing portion 14. In some embodiments, the sensitivity of the device may be reconfigured on the same body portion or may be reconfigured to a different body portion.

While shown and described with respect to FIG. 1 as having a single sensor 22 and signaling mechanism 20, in some embodiments the device can include any number of sensors and/or signaling mechanisms. For example, the device can include a first sensor to detect deviation in a first direction and a second sensor to detect deviation in a second direction. For another example, the device can include a first signaling mechanism to provide visual feedback (e.g., a light), a second signaling mechanism to provide audio feedback (e.g., a speaker) and/or a third signaling mechanism to provide haptic feedback (e.g., a vibrator).

A device 36 according to an embodiment is schematically illustrated in FIG. 2A. The device 36 can be structurally and/or functionally similar to the device 10 shown and described with respect to FIG. 1. Device 36 includes a housing with two separate portions. A first housing portion 38 includes a mercury tilt switch 30 (which can be structurally and/or functionally similar to the sensor 22 of FIG. 1), a vibrating element 32 and an LED light bulb 34 (each of which can be structurally and/or functionally similar to the signaling mechanism 20 of FIG. 1), and a magnet 42a (which can be structurally and/or functionally similar to the anchoring element 18a of FIG. 1). A second housing portion 40 includes a magnet 42b and a portion of a hook and loop fastener 44.

In some embodiments, the first housing portion 38 is spherical. In some embodiments, the second housing portion 40 is coin shaped, cylindrical or a rectangular prism. The first housing portion 38 can be removably and/or rotatably coupled to the second housing portion 40 using magnet 42a and magnet 42b.

According to an embodiment, the magnet 42a, serving as an anchoring element between the first housing portion 38 and the second housing portion 40, may freely reposition within the first housing portion 38.

In some implementations, the tilt (orientation or position) of the mercury tilt switch 30 changes with respect to the neutral position of the mercury tilt switch 30 as the user moves and/or rotates the first housing portion 38 with respect to the second housing portion 40. In some implementations, such repositioning alters the amount of tilt (or angular or rotational distance) between the neutral tilt switch position and deviated tilt switch position. In some implementations, repositioning and/or rotating the first housing portion 38 with respect to the second housing portion 40 calibrates or adjusts the amount of tilt between the neutral tilt switch position and deviated tilt switch position, thereby calibrating the sensitivity of the device.

Figure 2B:
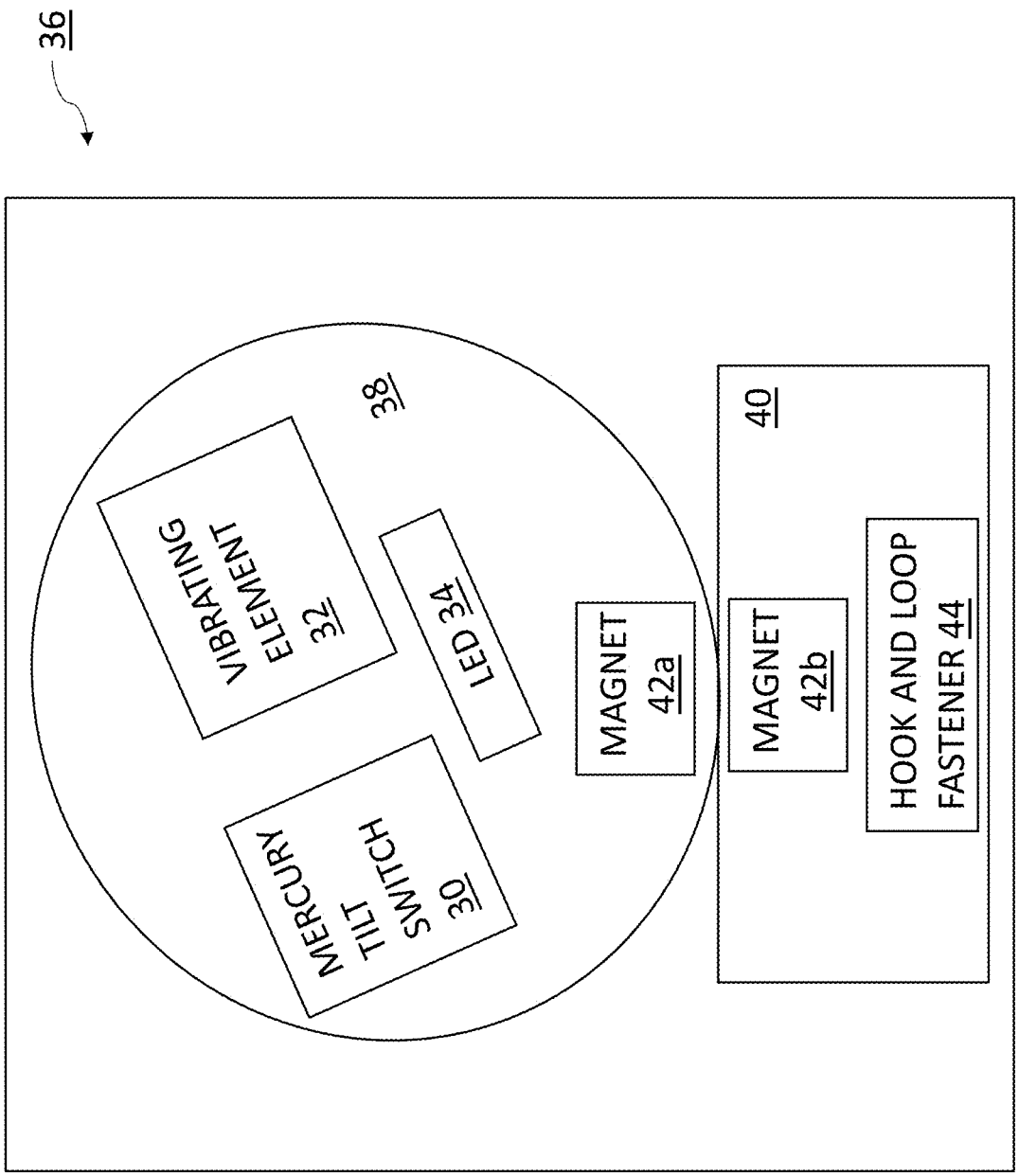
Figure 2E:
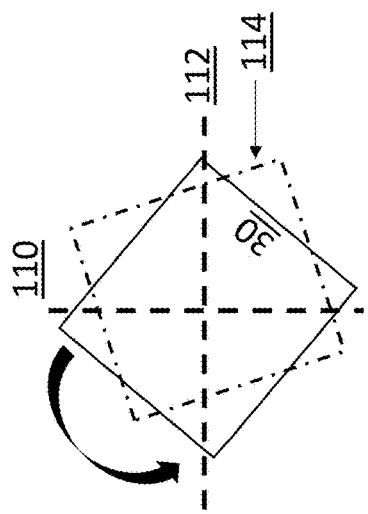
FIGS. 2C, 2D, and 2E are schematic illustrations of a tilt switch with respect to central axis 110 and longitudinal axis 112, the threshold for activation of the vibrating element and LED is outlined with dashed lines (alternating long/short dashes) 114, and the direction of rotation is indicated with a curved arrow, according to an embodiment.
Figure 2D:
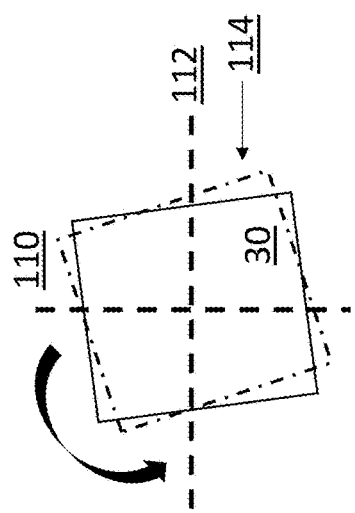
Figure 2C:
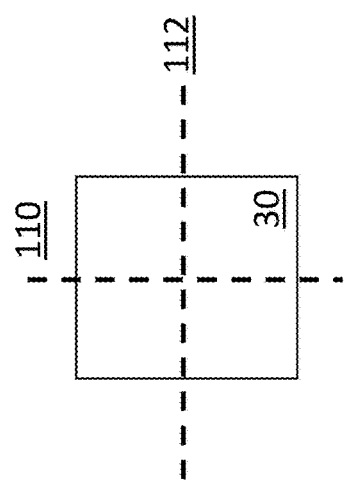

For example, as shown in FIGS. 2C and 2D, the neutral tilt switch position can be such that the mercury tilt switch 30 is centric (e.g., radially symmetrical) relative to a central axis 110 and the triggered tilt switch position can be such that the mercury tilt switch 30 is or can be eccentric (e.g., radially asymmetrical) relative to the central axis 110. In some implementations, the triggered tilt switch position activates the sensor and subsequently, the sensor provides electricity to the signaling mechanism, which provides feedback to the user of the detected muscle deviation.

In some implementations, repositioning allows the device to be positioned on different portions of the garment and calibrated according to a desired muscle position, where the desired muscle position is set as, for example, the neutral tilt switch position. In some implementations, the device is calibrated such that the amount of tilt between the neutral tilt switch position and triggered tilt switch position (e.g., a distance the tilt switch 30 is moved, tilted, or rotated from the neutral tilt switch position relative to the central axis 110) is decreased relative to a prior calibration, thereby increasing the sensitivity of the device to user position.

In some implementations, the device is calibrated such that the amount of tilt between the neutral tilt switch position and triggered tilt switch position is increased relative to a prior calibration, thereby decreasing the sensitivity of the device to user position.

In some implementations, repositioning alters the amount of tilt between the neutral tilt switch position and deviated tilt switch position (e.g., a distance the tilt switch 30 is moved, tilted, or rotated from the neutral tilt switch position relative to the central axis 110), allowing the device to be positioned on different portions of the garment and calibrated according a desired muscle position.

FIG. 2B, for example, shows the first housing portion 38 rotated with respect to the second housing portion 40. As shown, the magnet 42a has remained in contact with the magnet 42b to ensure the first housing portion 38 remains coupled to the second housing portion 48, but the angle of the mercury tilt switch 30 with respect to the magnet 42a and the second housing portion 48 has changed. This change allows the mercury tilt switch 30 to be calibrated and/or adjusted to meet the needs of the user and to ensure that the range of positions in which the mercury tilt switch 30 is in the first configuration (e.g., in an "off" position) is appropriate for the user's application.

While shown in FIG. 2B as being rotated along an axis, because the first housing portion 38 is spherical, the first housing portion 38 can be rotated with respect to the second housing portion 40 along all three axes. This allows flexibility for the user to effectively calibrate the device 36 for various positions, sensitivities and/or applications.

FIG. 2C, for example, shows a mercury tilt switch 30 with respect to central axis 110 and longitudinal axis 112. Central axis 110 is perpendicular to longitudinal axis 112.

FIG. 2D, for example, shows a mercury tilt switch 30 with respect to central axis 110 and longitudinal axis 112 as the user moves and/or rotates the first housing portion with respect to the second housing portion. The direction of rotation is indicated with a curved arrow and the threshold for activation of the vibrating element 32 and LED 34 is outlined with dashed lines (alternating long/short dashes) 114. In this example, the mercury switch has not deviated past the threshold and therein has not activated the vibrating element 32 and LED 34.

FIG. 2E, for example, shows a mercury tilt switch 30 with respect to central axis 110 and longitudinal axis 112 as the user moves and/or rotates the first housing portion with respect to the second housing portion. The direction of rotation is indicated with a curved arrow and the threshold for activation of the vibrating element 32 and LED 34 is outlined with dashed lines (alternating long/short dashes) 114. In this example, the mercury switch has deviated past the threshold and therein has activated the vibrating element 32 and LED 34.

In an embodiment, the user may calibrate the mercury tilt switch 30 such that the neutral configuration of the mercury tilt switch 30 is closer to the threshold 114 relative to a previously configured neutral configuration, thereby decreasing the amount of user deviation required to reach the second configuration of the device and activate the vibrating element 32 and LED 34.

In some embodiments, methods disclosed herein include positioning a device having a sensor on a user, wherein the sensor detects deviation from desired muscle position in the user. In some embodiments, the sensitivity of the device's sensor may be calibrated through rotating a first housing portion having at least one sensor and at least one signaling mechanism with respect to a second housing portion having an attachment element. In some embodiments, the at least one sensor senses the orientation of at least one body portion, and upon sensing deviation from desired muscle position, the at least one signaling mechanism generates predetermined feedback to the user, and in response to the feedback, the user can adjust the orientation of the deviated body portion to achieve desired muscle position. In some embodiments, the sensitivity of the device sensor may be adjusted and readjusted to dynamically detect deviations of muscle position. In some embodiments, the sensitivity of the device is adjusted by rotating the first housing portion with respect to the second housing portion.

Figure 3:
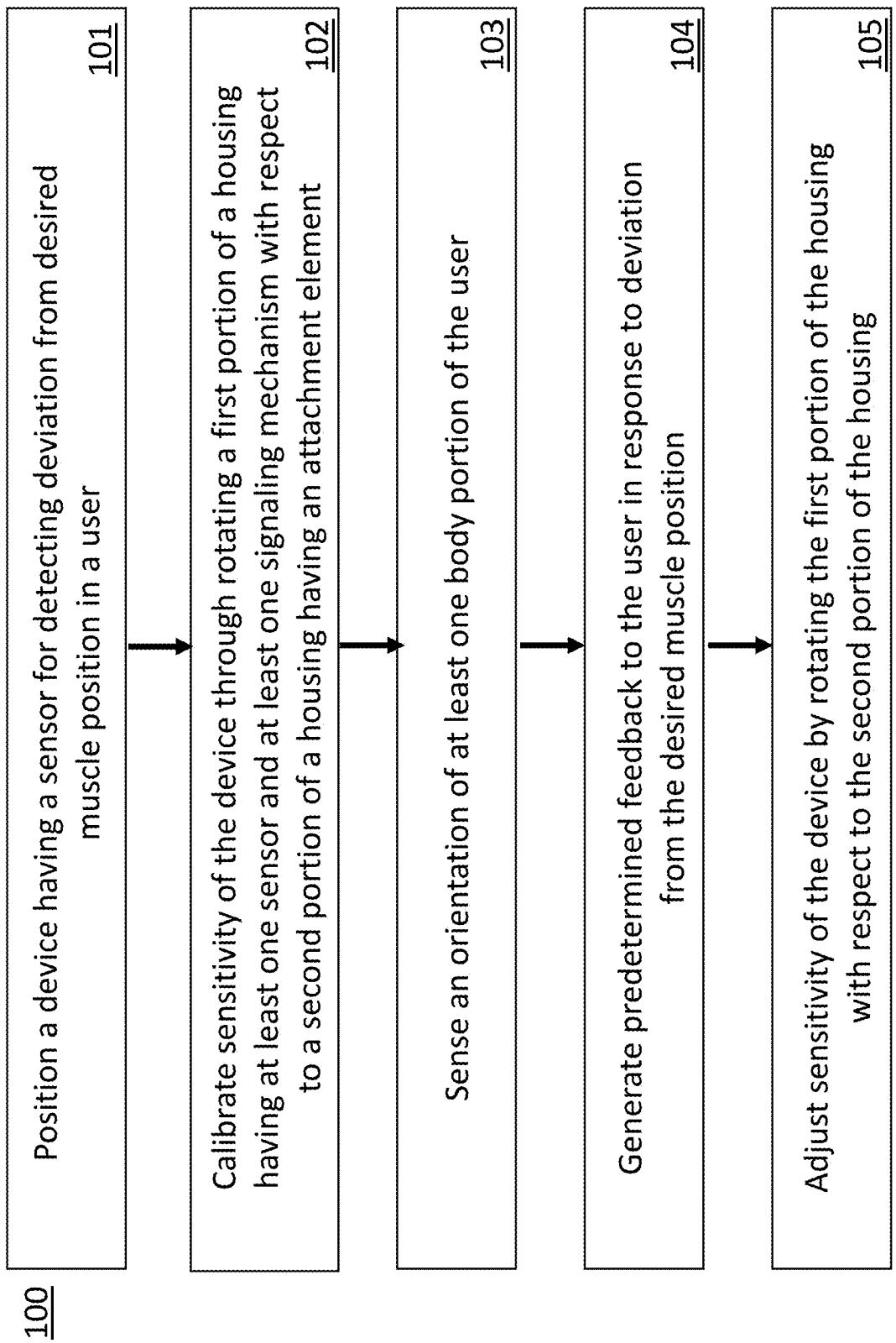
FIG. 3 is a flowchart illustrating a method of providing muscle position feedback, according to an embodiment.

FIG. 3 is a flowchart illustrating a method 100 for detection of muscle deviation in a user, according to an embodiment. The method 100 includes, at 101, the user positioning the device (e.g., structurally and/or functionally similar to device 10 of FIG. 1 and/or device 36 of FIG. 2A) having a sensor for detecting deviation from a desired muscle position in a user onto a garment via an attachment element. The user can fasten the device to the garment such that a second housing portion of the device is attached to the garment and a first housing portion of the device is coupled to the second housing portion.

At 102, the user can calibrate the sensitivity of the device through rotating the first housing portion having at least one sensor and at least one signaling mechanism with respect to the second housing portion having the attachment element. When positioning the device, the user can rotate the first portion with respect to the second housing portion such that when a body portion is in the desired muscle position, the sensor is not activated and the signaling mechanism does not receive electricity. The desired muscle position includes a range of positions that do not activate the sensor. To narrow or expand the range of positions that do not activate the sensor, the user may alter the angle of the sensor within the first housing portion with respect to the second housing portion, thus calibrating the sensitivity of the sensor to the range of positions which are desired and therein not detected.

The method 100 further includes, at 103, sensing an orientation of at least one body portion of the user. Specifically, for example, when the sensor is deviated outside of the range of desired positions, the sensor is activated into a second configuration such that electricity is sent to the signaling mechanism. The signaling mechanism is in turn also activated into a second configuration. The activation of the signaling mechanism into a second configuration, at 104, generates predetermined feedback to the user in response to the deviation outside of the range of desired muscle positions. In some implementations, the feedback includes a combination of a vibration and light from an LED light bulb. Upon receiving feedback from the device, the user may adjust their body portion to restore the angle of the sensor such that it returns to the first configuration and inactivates the signaling mechanism.

Upon returning the device to the first configuration, at 105, the user may rotate the first housing portion with respect to the second housing portion to adjust the sensitivity of the device. For example, the user may adjust the sensitivity of the device such that there is a narrower range of desired muscle positions, thereby increasing the sensitivity of the device. Conversely, the user may adjust the sensitivity of the device such that there is a wider range of desired positions that do not activate the sensor, thereby decreasing the sensitivity of the device.

In some embodiments, the generation of feedback through the signaling mechanism indicates a deviation from desired muscle position to the user. The user can adjust a body portion to a desired muscle position in response to the device feedback.

Figure 4:
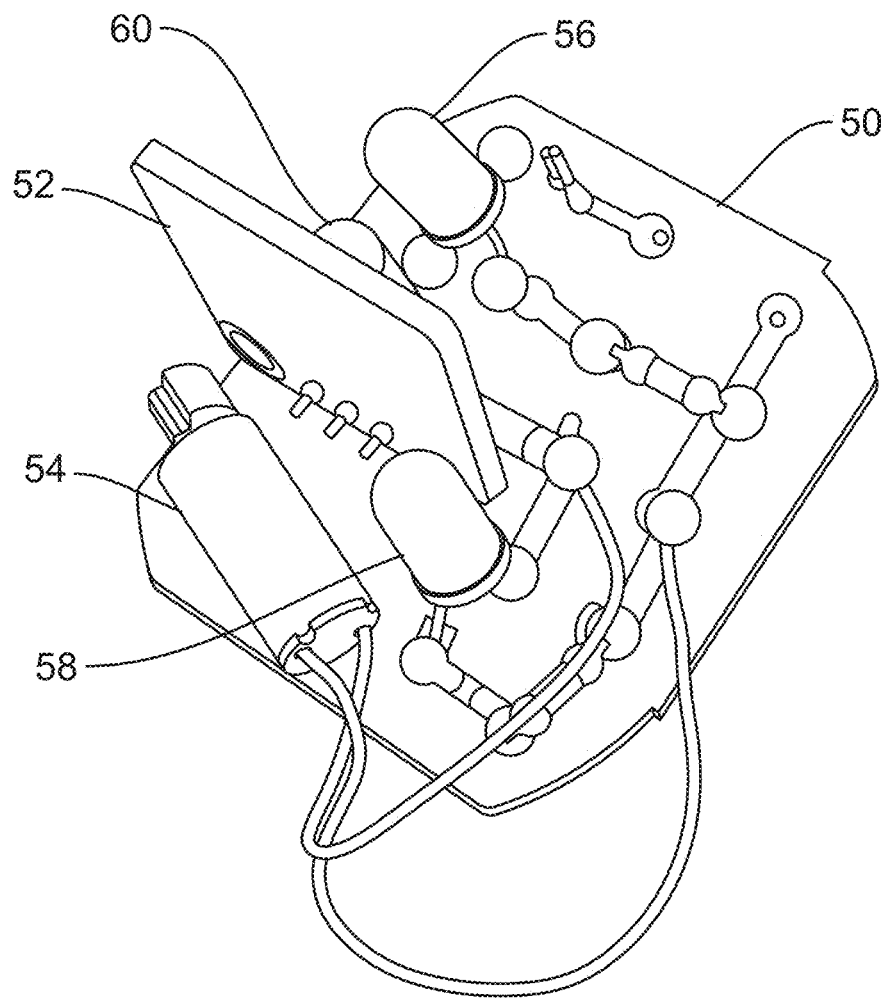
FIG. 4 illustrates a circuit board, according to an embodiment.

As illustrated in FIG. 4, according to an embodiment, provided within the first housing portion is a copper clad printed circuit board (PCB) 50, a battery 52 (power source), a vibrating element 54, LED light bulbs 56 and 58, a mercury tilt switch 60 (as a sensor), and a power switch (not shown). In some implementations, the LED light bulb 56 signals the power switch is in the "on" position (i.e., the device is functional) and LED light bulb 58 is a signaling mechanism electrically coupled to the vibrating element. Accordingly, in such implementations, the LED light bulb 56 is lit when the device is functional and the LED light bulb 58 is lit when a deviation is detected.

In some embodiments, the circuit may be a PCB etched with ferric chloride, an application-specific integrated circuit (ASIC), a microcontroller, or other processing device. As discussed above, when in the first configuration, the mercury tilt switch 60 acts as a switch in an "off" position and does not allow electrical current to flow from the battery 52 to the vibrating element 54 and/or LED light bulb 58. When the mercury tilt switch 60 is tilted and/or moved such that it is in the second configuration, the mercury tilt switch 60 acts as a switch in an "on" position and allows electrical current to flow from the battery 52 to the vibrating element 54 and the LED light bulb 58, thus activating the vibrating element and the LED light bulb 58 and alerting the user. After attaching the device to a user and calibrating the device to ensure that the mercury tilt switch 60 is in the correct position and/or at the correct angle, the device can detect deviation of the position of a user.

As illustrated in FIG. 5, according to an embodiment, a first housing portion 70 is secured to a second housing portion 72. In some embodiments, the mercury tilt switch (not shown) maintains a fixed position within the first housing portion 70. In some embodiments, the PCB 74 maintains a fixed position within the first housing portion 70 while the magnet 76 can move within the housing allowing the user to amend the configuration of the device.

Figure 6:
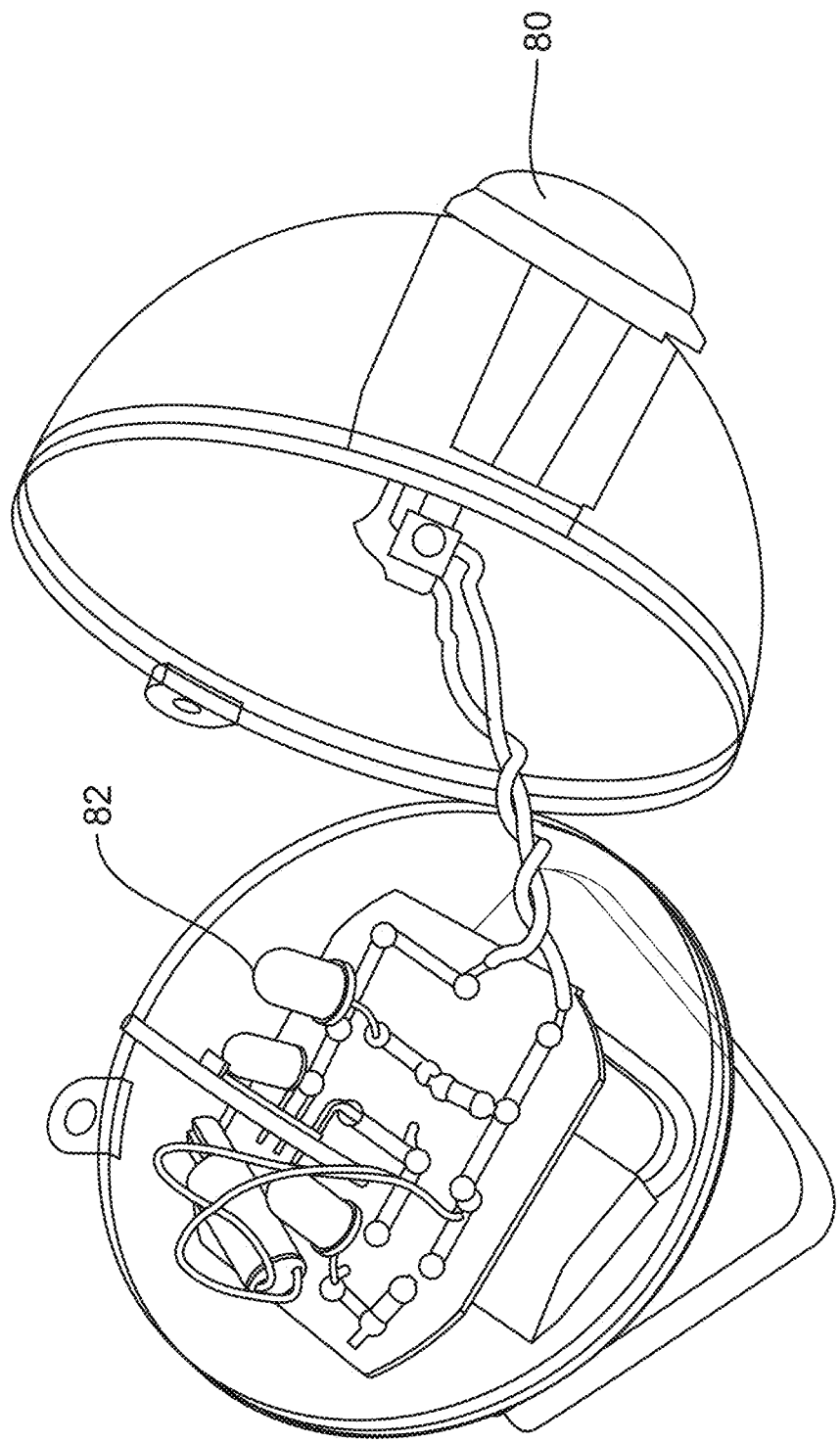
FIG. 6 illustrates a first housing portion having a circuit board, according to an embodiment.

As illustrated in FIG. 6, according to an embodiment, an LED light bulb 82 signals the power switch 80 is in the 'ON' position. As such, the user can identify when the device is operational. As discussed above, a second LED light bulb and/or a vibrator can be used to signal a deviation from a desired position. While shown as an LED light bulb 82, in other embodiments any other indicator (sound using a speaker, vibration using the vibrator, etc.) can be used to signal to the user that the device is operational.

Figure 7:
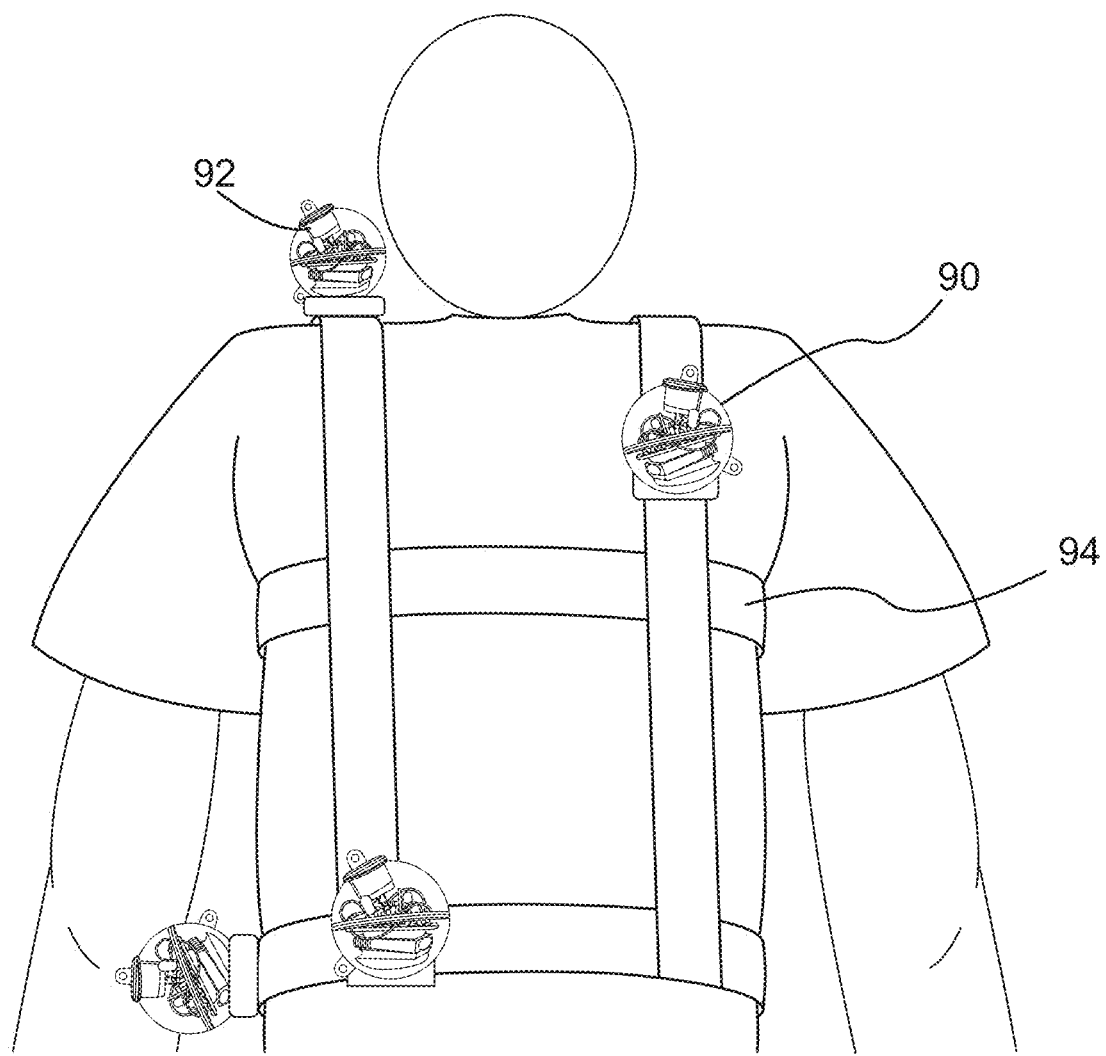
FIG. 7 illustrates a system having four devices in use, according to an embodiment.

As illustrated in FIG. 7, according to an embodiment, a system includes a first device 90 and a second device 92 positioned on a garment 94. The first device 90 detects deviation of muscle position in a first body portion and the second device 92 detects deviation of muscle position in a second body portion. The devices 90 and 92 can be structurally and/or functionally similar to the device 10 shown and described with respect to FIG. 1.

In some implementations, the system may include any suitable number of devices (e.g., 1, 2, 3, 4, 5, 6, 7, 8, 9, 10, etc. devices). In some implementations, each device may detect deviation of muscle position of a different body portion. In some embodiments, each device can be placed on different portions of the garment and calibrated to individually detect deviations of muscle positions. This allows a user to monitor the position of multiple body portions simultaneously.

In some embodiments, the garment 94 can include hooks or loops of a hook and loop fastener, or one or more straps, enabling the user to wear the device 10 strapped around a portion of their body. In some embodiments, the garment 94 can be an article of clothing, a brace, a vest, and/or the like.

In some embodiments, the attachment element 16 can secure the device on any suitable body portion of the user, including, but not limited to the head, hip, shoulder, pelvis, waist, chest, torso, arms, legs, abdomen, foot, ankle, hand, or wrist. In some embodiments, the device can be moved, repositioned, and/or rearranged by the user.

In some instances, the device can be used by a user diagnosed with a movement disorder. For example, in some instances the device can be used by a user that has been diagnosed with Cerebral palsy. For example, in some instances the device can be used by a user suspected to have a movement disorder, Cerebral palsy, and/or the like. Non-limiting examples of symptoms of Cerebral palsy include, for example, impairment of muscle tone, gross and fine motor functions, balance, control, coordination, reflexes, and posture, abnormal muscle tone, and/or unusual posture. In some instances, the device can be used by users looking to improve posture and/or rehabilitating from other medical conditions and/or injury.

In some instances, the present disclosure provides a device comprising at least one sensor and at least one signaling mechanism to detect deviation from a desired muscle position and generates feedback to a user in response to the deviation. For example, the device can be used by users with symptoms including, but not limited to, slouching, crouching, incorrect muscle use, overcompensating with the wrong muscle, overly using one side of the body, wrong alignment, hypotonia, hypertonia, dystonia, muscle spasms, abnormal neck or truncal tone, clonus, ankle/foot clonus, wrist clonus, and/or the like. In some embodiments, the symptoms described herein can be associated with a defect in movement, including situations without clear understanding of the underlying causes for the defect.

The device and methods of the present disclosure can be applied to non-movement disorders for which restoration of desired muscle positioning would be beneficial and/or therapeutic. Moreover, the device and methods of the present disclosure can be used to treat or prevent symptoms of movement disorders and/or to be used in orthopedic treatments. In some embodiments, the orthopedic treatments may take place before and/or after surgery.

As used in the description of the invention and the appended claims, the singular forms "a", "an", and "the" are intended to include the plural forms as well, unless the context clearly indicates otherwise.

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

The terms "user" or "subject" as used herein includes a human, primate, mouse, rat, dog, cat, cow, horse, goat, camel, sheep, a pig, preferably a human.

"Treat," "treating" or "treatment" as used herein also refers to any type of action or administration that imparts a benefit to a subject that has a disease or disorder, including improvement in the condition of the patient (e.g., reduction or amelioration of one or more symptoms), healing, etc.

The term "desired muscle position" as used herein refers to a position of muscle desired to be maintained by a user. For example, a desired muscle position can be an alignment that is a position of the musculoskeletal structure in which the body is balanced, wherein the ankles, pelvis, thorax, and head are aligned vertically so that from a side view they form a straight line. For another example, a desired muscle position can be further characterized by the ability of a muscle to function normally and/or maintain a normal length-tension relationship. The desired muscle position can be identified and/or determined by an individual, a health care provider, and/or the like and may be specific to a user and/or condition. The term "neutral position" when referring to a tilt switch or other sensor refers to a position of a tilt switch or sensor component of a device of the present disclosure which corresponds to the desired muscle position of the user. The term "deviated position" when referring to a tilt switch or other sensor refers to a position of a tilt switch or sensor component of a device of the present disclosure which corresponds to muscle position outside of the range of the neutral position configuration. Also as used herein, "and/or" refers to and encompasses any and all possible combinations of one or more of the associated listed items, as well as the lack of combinations when interpreted in the alternative (or).

Unless the context indicates otherwise, it is specifically intended that the various features described herein can be used in any combination. Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed.

It will also be understood that, as used herein, the terms example, exemplary, illustrative, and grammatical variations thereof are intended to refer to non-limiting examples and/or variant embodiments discussed herein, and are not intended to indicate preference for one or more embodiments discussed herein compared to one or more other embodiments.

Unless the context indicates otherwise, it is specifically intended that the various features described herein can be used in any combination.

What is claimed is:

1. A device, comprising:
   a first housing portion having a tilt switch, a vibrating element, and a visual indication device, the first housing portion being spherical; and
   a second housing portion rotatably coupled to the first housing portion, the second housing portion having an attachment element configured to couple the second housing portion to a user,
   the tilt switch fixedly mounted in the first housing portion and senses a change in position of the first housing portion,
   the tilt switch configured to detect deviation of a muscle position of the user relative to a desired muscle position of the user when the attachment element couples the second housing portion to the user,
   the vibrating element configured to provide a haptic indication and the visual indication device configured to provide a visual indication in response to the tilt switch detecting deviation from the desired muscle position of the user by a predetermined amount, the predetermined amount is configured to be adjusted through rotating the first housing portion with respect to the second housing portion.

2. The device of claim 1, wherein the second housing portion is coin shaped.

3. The device of claim 1, wherein the attachment element includes a portion of a hook and loop fastener.

4. The device of claim 1, wherein the first housing portion includes a first magnet, and the second housing portion includes a second magnet, the second housing portion being rotatably coupled to the first housing portion using the first magnet and the second magnet.

5. The device of claim 1, wherein the first housing portion is rotatably coupled to the second housing portion using at least one magnet.

6. The device of claim 1, wherein the first housing portion includes a first magnet, and the second housing portion includes a second magnet,
   the first magnet is configured to freely reposition within the first housing portion.

7. The device of claim 1, wherein deviation from a desired muscle position moves the tilt switch with respect to a predetermined axis associated with a neutral position.

8. The device of claim 7, wherein the rotating of the first housing portion with respect to the second housing portion alters a rotational distance between a neutral tilt switch position and a triggered tilt switch position, the triggered tilt switch position associated with the predetermined amount of deviation of the desired muscle position.

9. The device of claim 1, wherein a position of the tilt switch deviates with respect to a neutral tilt switch position as the first housing portion rotates with respect to the second housing portion.

10. The device of claim 9, wherein the rotating of the first housing portion with respect to the second housing portion alters a rotational distance between the neutral tilt switch position and a triggered tilt switch position, the triggered tilt switch position associated with the predetermined amount of deviation of the desired muscle position.

11. The device of claim 1, wherein the attachment element includes a portion of a fastener that is configured to removably couple, in a user-selected orientation, the second housing portion to a garment, the garment wearable by the user.

12. The device of claim 11, wherein the garment includes a portion of the fastener to removably couple the device to the user in a user-selected orientation when the user wears the garment.

13. The device of claim 12, wherein the fastener is at least one of a hook and loop fastener, a clip, a pocket, a pin, a buckle, snaps, grommets, or snap hooks.

14. A method, comprising:
   positioning, on a user, a device having a sensor including a tilt switch for detecting deviation from a desired muscle position in the user;
   calibrating sensitivity of the device through rotating a first housing portion with respect to a second housing portion, the second housing portion having an attachment element configured to attach the second housing portion to the user, the first housing portion having the sensor, a vibrating element, and a visual indication device, the first housing portion being spherical; and
   generating predetermined feedback through the vibrating element and the visual indication device to the user in response to deviation from the desired muscle position by a predetermined amount.

15. The method of claim 14, comprising:
   adjusting a positioning of the attachment element by removably coupling, using a fastener and in a user-selected orientation, the second housing portion to a garment wearable by the user.

16. The method of claim 15, wherein the fastener is at least one of a hook and loop fastener, a clip, a pocket, a pin, a buckle, snaps, grommets, or snap hooks.

17. A system, comprising:
a plurality of devices, each device from the plurality of devices being coupled to a user at a different body portion than the remaining devices from the plurality of devices,
each device from the plurality of devices includes:
- a spherical first housing portion having a tilt switch, a vibrating element, and a visual indication device; and
- a second housing portion rotatably coupled to the first housing portion, the second housing portion having an attachment element configured to couple the second housing portion to a body portion of the user, the tilt switch is configured to detect deviation of a muscle position of the user when the attachment element couples the second housing portion to the user,
the vibrating element is configured to provide a haptic indication and the visual indication device is configured to provide a visual indication in response to the tilt switch detecting deviation of the muscle position of the user by a predetermined amount, the predetermined amount is configured to be adjusted through rotating the first housing portion with respect to the second housing portion.

18. The system of claim 17, wherein a position of the tilt switch of each device from the plurality of devices changes with respect to a neutral tilt switch position as the user moves.

19. The system of claim 17, wherein the rotating of the first housing portion with respect to the second housing portion alters a rotational distance between a neutral tilt switch position and a triggered tilt switch position, the triggered tilt switch position associated with deviation of the muscle position by the predetermined amount.

20. The system of claim 17, wherein the attachment element of each device includes a portion of a fastener that is configured to removably couple, in a user-selected orientation, the second housing portion to a garment wearable by the user.

* * * * *